US005094220A

United States Patent [19]

Lacruche et al.

[11] Patent Number: 5,094,220

[45] Date of Patent: Mar. 10, 1992

[54] DEVICE FOR IMPROVING ELECTRICAL CONTACT BETWEEN AN ELECTRICAL CONDUCTOR AND AN ELECTRODE

[75] Inventors: Bernard Lacruche, Lyons; Jean-Paul Aschwanden, Corbas; Dominique Cathignol, Genas, all of France

[73] Assignees: Technomed International, Paris; INSERM, Paris Cedex, both of France

[21] Appl. No.: 541,483

[22] Filed: Jun. 21, 1990

Related U.S. Application Data

[63] Continuation of Ser. No. 148,759, Jan. 26, 1988, abandoned.

[30] Foreign Application Priority Data

Jan. 9, 1987 [FR] France ................................ 8701083

[51] Int. Cl.[5] ............................................ A61B 17/22

[52] U.S. Cl. ............................... 128/24 OEL; 439/14

[58] Field of Search ................. 128/24 EL; 439/1, 14, 439/15

[56] References Cited

U.S. PATENT DOCUMENTS 1,930,322 10/1933 Paulson ................................ 439/13
2,559,227 7/1951 Rieber .............................. 128/24 A
3,942,531 3/1976 Hoff et al. .......................... 128/328
4,420,198 12/1983 Zerlik .................................. 439/13
4,608,983 9/1986 Muller et al. ...................... 128/328
4,730,614 3/1988 Lacruche et al. .................. 128/328
4,741,702 5/1988 Yasumoto ............................ 439/13

FOREIGN PATENT DOCUMENTS 0124686 8/1984 European Pat. Off. .
0674147 1/1930 France ............................... 439/254
2247195 9/1975 France .
0647157 12/1950 United Kingdom .................. 439/13

*Primary Examiner*—Kyle L. Howell
*Assistant Examiner*—K. M. Pfaffle
*Attorney, Agent, or Firm*—Schechter, Brucker & Pavane

[57] ABSTRACT

The invention relates to a device for providing improved electrical contact between an electrical conductor and an electrode. The device is characterized in that it comprises a fixed position nut-forming contact element made of an electrically conductive material and including an axial bore through which the electrode passes, the electrical conductor terminating at the nut-forming element in the form of a connection tab. The nut-forming element advantageously comprises two half-disks for facilitating assembly and disassembly while providing improved electrical contact during operation.

24 Claims, 3 Drawing Sheets

DEVICE FOR IMPROVING ELECTRICAL CONTACT BETWEEN AN ELECTRICAL CONDUCTOR AND AN ELECTRODE

This is a continuation of U.S. application Ser. No. 07/148,159 filed Jan. 26, 1988 now abandoned.

BACKGROUND OF THE INVENTION

1. Field of the Invention

The invention relates essentially to a device for providing improved electrical contact between an electrical conductor and an electrode, the use of said device in any device for advancing an electrode, and the incorporation of said device for providing electrical contact in an apparatus for generating shock waves or high frequency pulses.

2. Prior Art

Apparatus for generating shock waves or high frequency pulses, among then "lithotriptors", have been known for many years. Such apparatus include a device for focusing pulses on a target and may be constituted, in particular, by a truncated elliptical reflector as described in U.S. Pat. No. 2,559,227 (Rieber).

A similar apparatus is described in patent document FR-A-2 247 195 and U.S. Pat. No. 3,942,531.

The pulses or shock waves are generated by an electric arc or discharge between two electrodes which may be made of a highly conductive material such as copper or brass, and which are mounted on insulating supports.

In general, the discharges generated at the electrodes are accompanied by metal being torn away therefrom, thereby causing the electrodes to wear rapidly, which means that they need replacing relatively frequently.

In order to counter this wear, proposals have already been made in patent document EP-A-124 682 and commonly assigned U.S. Pat. No. 4,608,983 for a device which advances electrodes, said device including a control member which controls simultaneous movement of the electrodes towards or away from each other by means of rotation in one direction or in the opposite direction.

Other electrode-advancing devices are described in commonly assigned U.S. Pat. No. 4,370,614.

U.S. Pat. No. 4,780,614 describes a device for advancing an electrode in which the supply of electrical current from a current source is provided by a conductor which terminates in an electrically conductive element which presses permanently in slidable manner against the electrode-carrier element which is likewise electrically conductive, thereby providing a sliding electrical contact.

However, the present inventors have observed that such a design of an electrical contact complicates assembling and disassembling electrode-carrier elements and their electrodes.

In addition, by virtue of the sliding electrical contact, surface oxidation of the respective sliding contact surfaces may take place, thereby reducing electrical conductivity, and this surface oxidation effect increases when the sliding contact occurs close to the heads of the electrodes. Electrical conductivity may also be reduced if the electrodes become dirty through electrode displacement, either because of the lubricant used, or else because of liquid coming from the liquid-filled cavity in which at least a portion of each electrode is immersed.

Thus, one aim of the invention is to solve a new technical problem consisting in providing a device capable of ensuring improved electrical contact between an electrical conductor for feeding electrical current and an electrode, which device is of simple design and facilitates assembly and disassembly of the the electrode-carrier elements and their electrodes.

Another aim of the present invention is to solve a novel technical problem consisting in providing a device to insure improved electrical contact and which automatically cleans the electrical contact surfaces, thereby giving rise to electrical conductivity which is maintained substantially perfectly at the electrical contact.

Another aim of the invention is to solve a novel technical problem consisting in providing a solution for avoiding the dirtying of the electrical contact by a lubricant or by a liquid coming from a liquid-filled cavity in which at least a portion of the electrode and/or its electrode-carrier element is immersed.

Preferably, these novel technical problems should be solved in such a manner as to be useable in any device for advancing an electrode, and in particular in a device for advancing electrodes constituting a portion of an apparatus for generating shock waves or high frequency pulses, thereby making it possible to increase the effectiveness with which targets such as lithiases or living tissues are destroyed.

These novel technical problems are solved for the first time in satisfactory manner by the present invention by providing a solution of relatively low cost which is largely compensated by a significant improvement in productivity; by an improvement in electrical conductivity during multiple utilizations of the electrodes; and finally by an increase in the effectiveness of target destruction when used in apparatus intended for destroying targets by generating electric arcs or discharges.

SUMMARY OF THE INVENTION

Thus, in a first aspect, the present invention provides a device for providing improved electrical contact between an electrical conductor for feeding electrical current and forming a portion of an electrical current feed connection, on the one hand and an electrode or its electrically conductive electrode-carrier element mounted to move in an insulating support, on the other. The device of the invention comprises permanent electrical contact means interposed between the electrical conductor and the electrode or its electrode-carrier element, characterized in that said permanent electrical contact means comprise a fixed position nut-forming element made of electrically conductive material and including an axial bore through which the electrode or its electrode-carrier element passes.

Preferably, the nut-forming element is fixed to an electrically conductive connection tab by any appropriate and advantageously electrically conductive means such as a screw, said connection tab being embedded in the insulating support and forming a portion of the electric current feed connection to the electrode or its electrode-carrier element.

In accordance with another particularly advantageous characteristic of the invention, the above-mentioned axial bore is threaded and the electrode or its electrode-carrier element includes a corresponding thread extending over an appropriate zone covering the extreme displacement positions of the electrode or its carrier element. Preferably, this threading is continuous so as to provide electrical contact over as large an area as possible.

In accordance with another particularly advantageous characteristic of the invention, the nut-forming element comprises two complementary half-disks.

Advantageously, each half-disk includes at least one slot, and preferably two diametrically opposite circumferential slots, which lie in a common plane in such a manner as to come into coincidence, preferably in pairs, when the two half-disks are assembled; at least one of the half-disks, and preferably both of them, including a centering plate of a size corresponding to a pair of coincident slots, with one portion of the plate being fixed in one half-disk slot bearing the plate and with the remaining portion of the plate being inserted in the aligned slot of the other half-disk.

Preferably, the other each half-disk also includes a plate, with the two plates diametrically opposite and symmetrically fixed about the center of the nut-forming element.

In a particular embodiment, each plate is in the form of a truncated sector of a disk.

In accordance with a particularly advantageous characteristic of the invention, the nut-forming element has an outer annular housing in which resilient return means are received, tending to clamp the two half-disks into contact against each other, e.g. a helical spring mounted in traction.

It can thus be understood that the above-mentioned technical advantages are obtained in a manner which is not obvious and is completely unexpected, namely: a significant improvement in productivity by virtue of the ease with which electrode-carrier elements and their electrodes can be assembled and disassembled; a considerable improvement in electrical conductivity during operation, by maintaining the initial electrical conductivity; and in addition the electrical contact is cleaned automatically, in particular by virtue of the thread of the nut-forming element cooperating with the thread of the electrode or its electrode-carrier element; and finally by avoiding the electrical contact being dirtied by a lubricant or by a liquid coming from the liquid-filled cavity in which at least a portion of the electrode or its carrier element is immersed, by virtue of the electrical contact being provided at the rear end of the electrode or its carrier element a long way from the device for controlling the advance of the electrodes.

It can thus be understood that the invention may provide a decided technological advance enabling it to be used in any device for advancing an electrode and in particular in an advancing device forming a portion of an apparatus for generating shock waves or high frequency pulses, with such utilization constituting an integral portion of the invention.

Finally, according to another aspect of the invention, the invention provides a generator of shock waves or high frequency pulses comprising the device conventionally including two electrodes arranged to generate an electrical arc or discharge therebetween, thus generating said shock waves or pulses, with at least one of said two electrodes being displacably mounted by means of a device for advancing the electrode, the apparatus being characterized in that it includes a device for providing electrical contact as defined above.

Other aims, characteristics and advantages of the invention appear more clearly in the light of the following description made with reference to the accompanying drawings which show the presently preferred embodiment of the device for providing improved electrical contact in accordance with the invention, said device being shown in its preferred utilization in an apparatus for generating shock waves or high frequency pulses, which apparatus is given purely by way of illustration and is not to be construed as limiting in any way the scope of the invention.

DESCRIPTION OF PREFERRED EMBODIMENT

Figure 1:
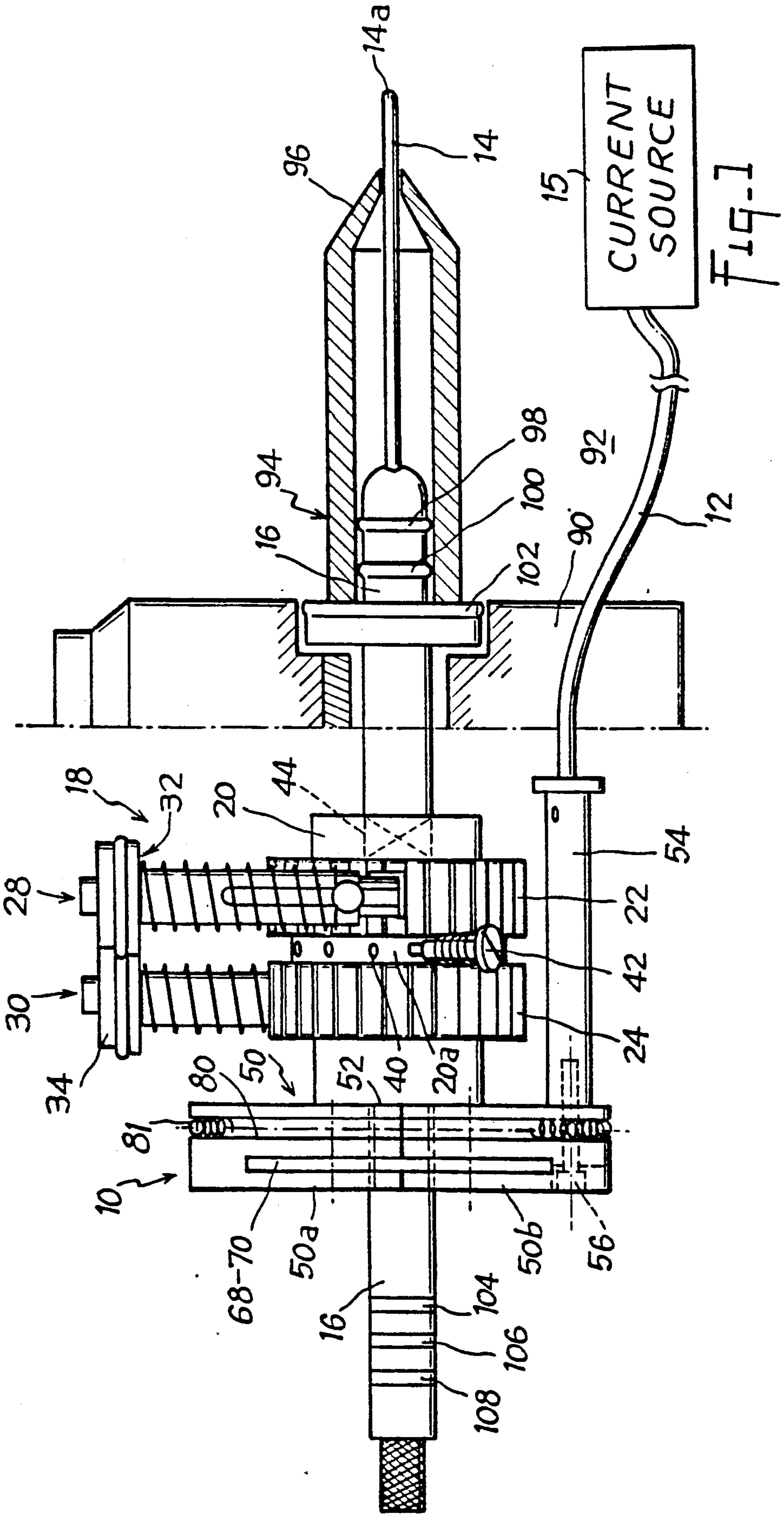
FIG. 1 is an elevational view, partly in section, of the presently preferred embodiment of a device for providing improved electrical contact in accordance with the invention, said device being used in a device for advancing an electrode which is itself incorporated in an apparatus for generating shock waves or pulses which is represented diagrammatically by the wall of the cavity in which said shock waves or pulses are generated.
Figure 2:
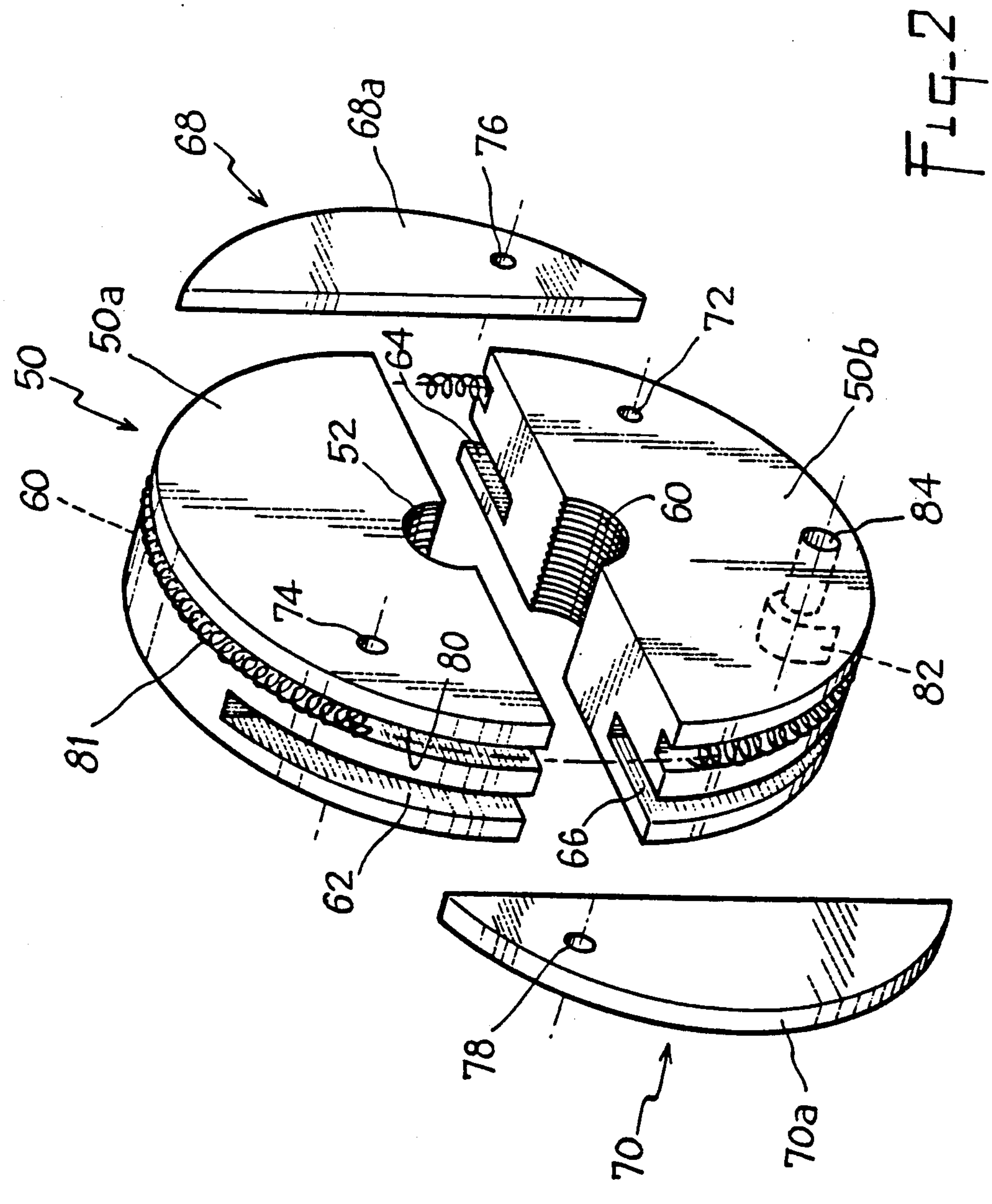
FIG. 2 is an exploded view of the nut-forming element which constitutes one of the essential parts of the device in accordance with the present invention.
Figure 3:
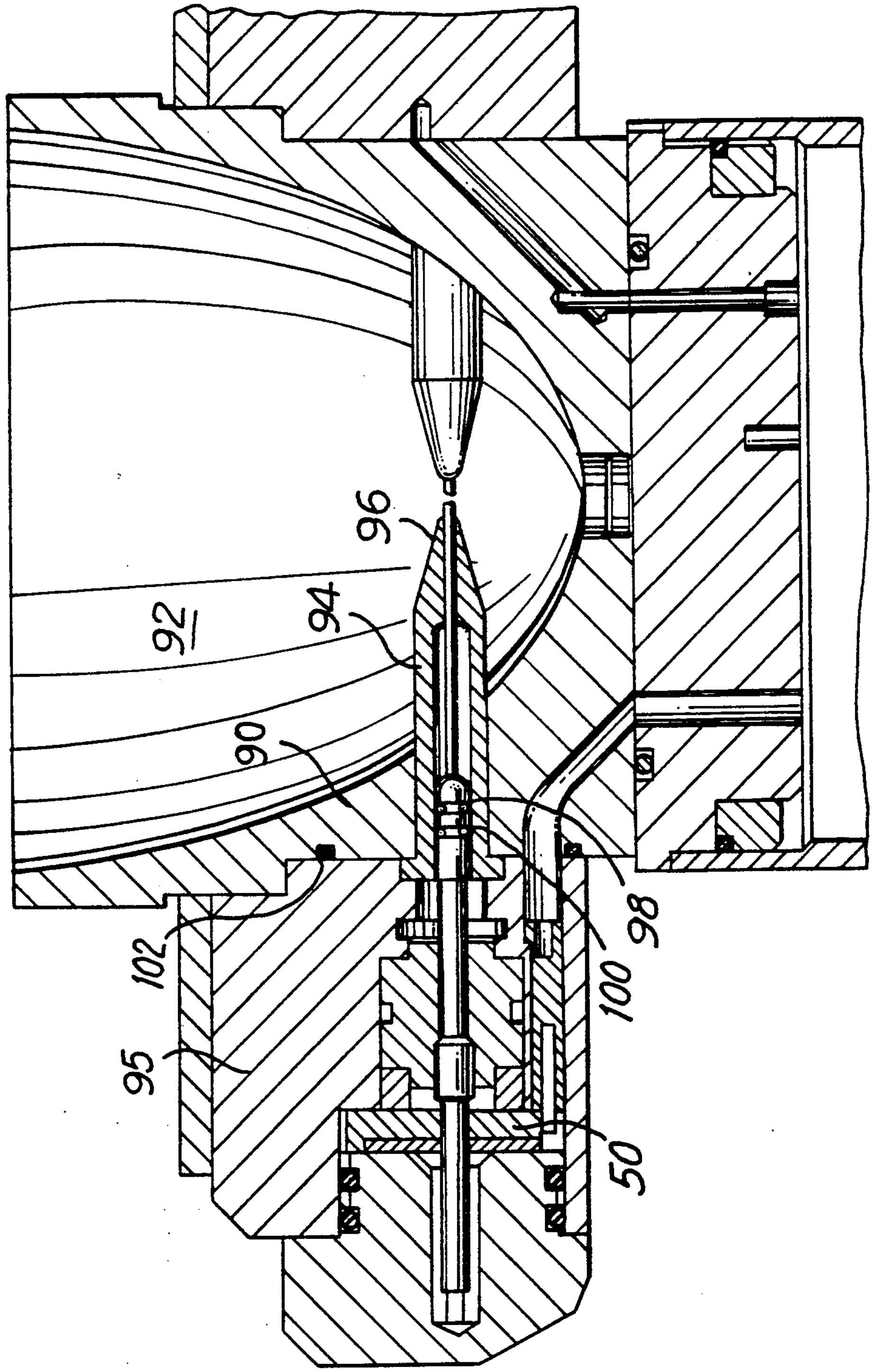
FIG. 3 is a view similar to FIG. 1, but showing in greater detail the preferred apparatus in which the invention is employed.

With reference to FIGS. 1–3 a device in accordance with the present invention is designated by an overall reference number 10. The device 10 provides electrical contact between an electrical conductor designated by an overall reference number 12 and forming a portion of a power supply connection for feeding electrical current from a current source 15 and an electrode 14, or more precisely in this case an electrode-carrier element 16, which carries the electrode 14 per se.

The device 10 for providing electrical contact is shown herein in use in a device 18 for advancing the electrode 14, or more precisely for advancing the electrode-carrier element 16.

The device for advancing the electrodes is, for example, as described and shown in U.S. Pat. No. 4,730,614, and it comprises a wheel 20 provided with two oppositely-directed sets of teeth 22 and 24 controlled by two control means 28 and 30 lying in the planes of the teeth on either side of the wheel 20. In this case, the control means 28 and 30 comprise two pistons 32 and 34 under hydraulic or pneumatic control, for example, and which are incorporated in corresponding piston bodies. For a more detailed description, reference may be made to said patent the content of which are hereby incorporated herein by reference.

The two sets of teeth 22 and 24 may be spaced apart so as to leave a zone 20*a* of surface between the sets of teeth 22 and 24 and including position-locking notches 40 which cooperate with a locking plunger 42. These locking notches may be simply constituted by hollows which are clearly visible in FIG. 1.

It will be observed that the electrode-carrier element 16 is constrained to rotate with, but is free to move in translation relative to, the wheel 20, and that the wheel 20 is provided, for this purpose, with an axial bore 44 of polygonal cross-section (in this case square) which cooperates with a corresponding square portion of the electrode-carrier element 16.

In accordance with the invention, the device 10 for providing electrical contact comprises an element 50 which constitutes a fixed position nut, which is made of electrically conductive material, and which constitutes the means for providing permanent electrical contact between the electrical conductor 12 and the electrode-carrier element 16. This nut-forming element 50 has an axial bore 52 through which the electrode passes, and more precisely in the present case through which the electrode-carrier element 16 passes, and it may also be observed that the electrical conductor 12 conveys electrical current right up to the nut-forming element 50.

Advantageously, the nut-forming element 50 is fixed on an electrically conducting connection tab 54 by any appropriate means which are advantageously electrically conductive, for example by means of a screw 56. This connection tab 54 is embedded in the mass of insulating material in which the electrode-carrier element and the control device 18 are movably mounted. This connection tab 54 naturally constitutes a portion of the power supply connection arrangement for feeding electrical current to the electrode-carrier element 16.

Preferably, the axial bore 52 is threaded and has a thread 59 which is clearly visible in FIG. 2, while the electrode-carrier element has a corresponding thread (not shown) covering an appropriate zone and extending between the extreme displacement positions of the electrode-carrier element 16. Each thread is preferably continuous so as to provide electrical contact over a large surface area, however the threads could be discontinuous, like other discontinuous threads known to the person skilled in the art.

In accordance with a particularly advantageous characteristic of the invention, the nut-forming element 50 is constituted by two complementary half-disks 50*a* and 50*b*.

Each half-disk 50*a* and 50*b* preferably includes at least one slot 60, 64, respectively and preferably each half-disk includes two diametrically opposite slots 60, 62 and 64, 66 respectively. These slots are disposed in a common axial plane as can clearly be seen in FIG. 2, so as to coincide (preferably in pairs e.g. 60 with 64; and 62 with 66), when the half-disks 50*a* and 50*b* are assembled. At least one of the half-disks, and preferably both of them as shown, has a centering plate 68, 70 having a size which corresponds with the size of a pair of coincident slots. A portion 68*a*, 70*a* of each plate 68, 70 is fixed in one of the slots of the plate-carrying half-disks by any appropriate fixing means such as a pin passing through an orifice 72, 74 in the half-disks 50*a*, 50*b* and also through aligned orifices 76, 78 plates in the 68, 70. It will be understood that the remaining portion of the plate is inserted in the slot 64 for the plate 68 or in the slot 62 for the plate 70 of the other half-disk 50*a* or 50*b*.

Preferably, and as shown, both plates 68 and 70 are disposed in diametrically opposite positions and are fixed symmetrically about the center of the nut-forming element, thereby simplifying interconnection of the two half-disks 50*a* and 50*b*. Advantageously, each of the plates 68, 70 is in the form of a truncated sector of a disk, as can clearly be seen in FIG. 2.

In accordance with another advantageous characteristic of the invention, the nut-forming element 50 has an annular recess 80 on its circumference for receiving resilient return means tending to hold the two half-disks 50*a* and 50*b* in contact with each other, e.g. a helical spring mounted in traction. A helical spring of shorter total length than the circumference of the annular housing 80 can thus be taken and its ends can be interconnected over a few turns so as to form an annular helical spring which is then stretched prior to being placed in the annular housing 80, in which it then exerts a compression force urging the two half-disks 50*a* and 50*b* towards each other.

FIG. 2 also shows that one of the two half-disks 50*a* and 50*b*, and in this case the half-disk 50*b*, includes a notch 82 forming a housing in which the connection tab 54 is fixed, said notch communicating with orifice 84 through which a fixing means 56, such as a screw is passed from the opposite face of the half-disk.

Naturally, the nut-forming element 50 is made of an electrically conductive material, and thus preferably of copper, although other electrically conductive materials could be used.

As mentioned above, the device 10 for providing electrical contact in accordance with the invention is preferably used in combination with a device 18 for advancing an electrode 14, the devices 10 and 18 both being housed in an insulating housing 95 which is well-known in the art as disclosed, for example, by U.S. Pat. No. 4,730,614 to Lacruche et al. best shown in FIG. 3. The electrode 14, and more precisely the electrode-carrier element 16 shown in FIG. 1, is mounted on the wall 90 of a device for generating and focusing pulses on a target focus, which device is preferably in the form of a truncated elliptical reflector of the type described by Rieber in U.S. Pat. No. 2,559,227. Thus, such a truncated elliptical reflector conventionally comprises two electrodes 14 which are advantageously identical and which are arranged to generate an electrical arc or discharge there-between. In general, said pulses are generated at the internal focus of the electrical reflector so that the electrodes are disposed in the immediate vicinity of said internal focus, thus enabling the pulses to be focused on the other focus of the ellipsoid at which the target to be destroyed is located. For a more detailed description of the operation of such apparatus, reference should be made to the above-mentioned documents.

The elliptical reflector, of which a portion of the wall 90 is best seen in FIGS. 1 and 3; is made of an electrically conductive material, and it is therefore necessary to insulate the electrode 14 and the electrode-carrier element 16 from the wall 90 by interposing an insulating support 94 about the electrode 14 as shown in FIGS. 1 and 3. The insulating support is substantially tubular in shape and is terminated by a conical front portion 96 which tapers towards the point of electrode 14 in order to completely insulate the electrode 14 as close as possible to its end 14*a*.

Given that the cavity 92 is filled with a liquid, advantageously with water, it is naturally necessary to provide sealing gaskets 98, 100, 102, 104, 106, and 108.

It will be understood from the above that the electrical contact nut-forming element 50 is fixed in position by virtue of the connection tab 54 which is embedded and therefore held in a fixed position in the insulating support surrounding the device as a whole. Thus, the action of the control device 18 causes the wheel 20 to rotate while the fixed position nut-forming element 50 cooperates by means of its own thread 59 with a corresponding screw-forming thread on the electrode-carrier element 16, thereby causing the electrode-carrying element 16 to advance or to retract as a function of the direction of rotation imparted thereto by the advance device, i.e., depending on which of the two pistons 32 or 34 is actuated.

Electrical current is permanently provided by virtue of the clamping effect due to the resilient return element 81 which as noted may be a helical spring. In addition, the electrical contact is automatically cleaned because of the thread on the nut-forming element 50 cooperating with the thread on the electrode-carrying element, thereby removing oxidized particles or any other interferring particles such as dust or the like.

Further, since the nut-forming element 50 constituting an electrical contact element is mounted at the rear portion of the electrode-carrier element 16 as far as possible from the leading end 14*a* of the electrode 14, it is possible to avoid the electrical contact being dirtied by a lubricant or by a liquid coming from the cavity 92. It may also be observed here that the control device 18 is interposed between the nut-forming contact element 50 and the electrode 14.

Further, by virtue of the nut-forming contact element 50 being made from two half-disks 50*a* and 50*b* which are clamped together by clamping means constituted by resilient return means 81, flexible clamping is obtained which fits exactly to the various possible diameters of the electrode-carrier element 16, thereby preventing the electrode-carrier element 16 from jamming in the nut-forming element 50.

Further, by virtue of this nut-forming element structure, it becomes very easy to assemble and disassemble the electrode-carrier elements 16 together with their electrodes 14, thus improving productivity.

Thus, all of the above-mentioned decisive technical advantages are obtained.

Also, a completely unexpected and non-obvious additional advantage of the invention lies in the fact that since the nut-forming electrical contact element 50 is fixed in position (since it is fixed in the insulating support by means of the connection tab 54 which is embedded in the mass of the insulating support), and since it includes a thread 59, the nut-forming element 50 is thus integrated in any system for advancing the electrode 14 and its electrode-carrier element 16 by constituting the fixed position nut-forming portion required for obtaining lateral displacement (advancement or retraction) of the electrode-carrier element under the effect of the wheel 20 being rotated by one of the pistons 32, 34. In this way, the thread 59 of the nut-forming electrical contact element 50 also performs the function of the nut-forming thread 170 of the insulating support 112*b* shown in FIGS. 3 and 4 of U.S. Pat. No. 4,730,614.

Naturally, the invention includes any means that constitute technical equivalents of the means described and also various combinations thereof.

We claim:

1. In a device for providing an improved electrical contact between an electrical conductor and an electrode member, said electrode member having an electrically conductive electrode carrier element mounted in an insulating housing for movement relative thereto, wherein the improvement comprises control means for controlling the rotation of the electrode member, a fixed position nut-forming element made of electrically conductive material interposed in electrical conductive relation between said electrical conductor and said electrode member for establishing permanent electrical contact therebetween, said nut-forming element defining an axial bore through which said electrode member passes and rotates; means for electrically connecting said electrical conductor to said nut-forming element; and means for effecting axial movement of said electrode member in said bore and relative to said insulating housing upon rotation of said electrode member by said control means.

2. A device according to claim 1, wherein said means for electrically connecting the electrical conductor to the nut-forming element comprises an electrically conductive tab imbedded in said insulating housing.

3. A device according to claim 1, wherein the nut-forming element comprises two complementary half-disks, and means for joining said half-disks together for defining said axial bore.

4. A device according to claim 3, wherein said means for joining said half-disks together comprises each half-disk having at least a first circumferential slot, said slots in said first and second half-disks being aligned when the half-disks are joined for defining said axial bore, and a first centering plate dimensioned for seating in said aligned slots, and means for securing said plate to one of said half-disks when said plate is seated in said aligned slots.

5. A device according to claim 4, wherein said means for joining said half-disks together further comprises each of said first and second half-disks having second circumferential slot, said second slots also being aligned when said half-disks are assembled for defining said axial bore, and further comprising a second centering plate dimensioned for seating in said aligned second slots and means for securing said second plate to at least one of said half-disks when said second plate is seated in said aligned second slots, whereby said centering plates are fixed symmetrically about the axis of the nut-forming element.

6. A device according to claim 4, wherein both centering plates are in the form of a truncated sector of a disk.

7. A device according to claim 3, wherein the nut-forming element has an annular groove on the outside thereof, and further comprising resilient means received in said groove for urging the two half-disks together.

8. A device according to claim 1, wherein said means for effecting axial movement comprises, said axial bore being internally threaded, said electrode member being adapted to move axially in said bore over a defined distance and including a corresponding externally threaded portion of sufficient axial length for mating with said internal thread of said axial bore as said electrode member moves over said defined distance, said mating of said externally threaded portion of said electrode member with said internally threaded bore of said nut-forming element effecting axial movement of the electrode member upon rotation.

9. A device according to claim 8, wherein said means for effecting axial movement further comprises means for rotating said electrode member.

10. A device according to claim 1, wherein said nut-forming element comprises a portion of said means for effecting axial movement of said electrode member.

11. In a device for use in an apparatus of the type comprising an electrode member connected to an electrical current supply by an electrical conductor; said apparatus further including control means for rotating said electrode member, said device providing improved electrical contact between said electrical conductor and said electrode member, said electrode member being mounted in an insulating housing for axial movement relative thereto, wherein the improvement comprises a nut-forming element made of electrically conductive material fixedly mounted to said insulating housing and interposed in electrical conducting relation between said electrical conductor and said electrode member for establishing permanent electrical contact therebetween, said nut-forming element defining an internally threaded axial bore through which said electrode member passes and rotates; and means for electrically connecting said electrical conductor to said nut-forming element, said electrode member being movable axially in said bore over a defined distance and including a corresponding externally threaded portion of sufficient axial length for mating with said internal thread of said axial bore as said electrode member moves over said defined distance, axial movement of said electrode member being effected upon rotation of said electrode member by said control means as a consequence of said mating of said externally threaded portion of said electrode member with said internally threaded bore of said fixedly mounted nut-forming element.

12. In an apparatus for generating shock waves or high frequency pulses, the apparatus being of the type which focuses said shock waves or pulses on a target and includes an insulating housing for movement relative thereto, a pair of spaced apart electrode members and a high voltage source for supplying a high voltage electrical current to said pair of spaced apart electrode members for generating an electrical arc through electrical discharge therebetween, and an electrical contact connecting said high voltage source to one of said electrode members, thus generating said shock waves or pulses, with at least one of said two electrode members being mounted for movement relative to the other, wherein the improvement comprises means for providing improved electrical contact between said electrical conductor connected to said high voltage source and one of said electrode members, said means comprising a nut-forming element made of electrically conductive material fixedly mounted to said insulating housing and interposed in electrical conducting relation between said electrical conductor and said electrode member for establishing permanent electrical contact therebetween, said nut-forming element defining an axial bore through which said electrode member passes and rotates; means for electrically connecting said electrical conductor to said nut-forming element, and means for effecting axial movement of said electrode member in said bore and relative to said insulating housing upon rotation of said electrode member.

13. The apparatus of claim 12, wherein said apparatus for focusing said shock waves or pulses on a target comprises a truncated elliptical reflector having an inner focus where the electrical arc is generated, and wherein a target coincides with a second focal point of said elliptical reflector located outside said truncated elliptical reflector.

14. A device according to claim 12, wherein said means for electrically connecting comprises an electrically conductive connecting tab embedded in the insulating housing and joined to said nut-forming element, said tab connecting said electrical conductor to said nut-forming element.

15. A device according to claim 12, wherein the nut-forming element comprises two complementary half-disks, and means for joining said half-disks together for defining said axial bore.

16. A device according to claim 15, wherein said means for joining said half-disks together comprises each half-disk having at least a first circumferential slot, said slots in said first and second half-disks being aligned when the half-disks are joined for defining said axial bore, and a first centering plate dimensioned for seating in said aligned slots, and means for securing said plate to one of said half-disks when said plate is seated in said aligned slots.

17. A device according to claim 16, wherein said means for joining said half-disks together further comprises each of said first and second half-disks having second circumferential slot, said second slots also being aligned when said half-disks are assembled for defining said axial bore, and further comprising a second centering plate dimensioned for seating in said aligned second slots and means for securing said second plate to at least one of said half-disks when said second plate is seated in said aligned second slots, whereby said centering plates are fixed symmetrically about the axis of the nut-forming element.

18. A device according to claim 16, wherein both centering plates are in the form of a truncated sector of a disk.

19. A device according to claim 15, wherein the nut-forming element has an outer annular groove on the outside thereof, and further comprising resilient means received in said groove for urging the two half-disks together.

20. A device according to claim 12, wherein said tab is fixedly mounted in said insulating support and said nut-forming element is connected to said tab and comprises part of said means for affecting axial movement.

21. A device according to claim 20, wherein said means for effecting axial movement comprises, said axial bore being internally threaded, said electrode member being movable axially in said bore over a defined distance, said electrode member including a corresponding externally threaded portion of sufficient axial length for mating with said internal thread of said axial bore as said electrode member moves over said defined distance, said mating of said externally threaded portion of said electrode member with said internally threaded bore of said nut-forming element effecting axial movement of the electrode member upon rotation.

22. A device according to claim 21, wherein said means for effecting axial movement further comprises means for rotating said electrode member.

23. A device according to claim 12, wherein said nut-forming element comprises a portion of said means for effecting axial movement of said electrode member.

24. In a device for providing an improved electrical contact between an electrical conductor and an electrode member, said electrode member having an electrically conductive electrode-carrier element mounted in an insulating housing for movement relative thereto, wherein the improvement comprises control means for rotating the electrode member; a fixed position nut-forming element made of electrically conductive material fixedly mounted to said insulating housing and interposed in electrical conductive relation between said electrical conductor and said electrode member for establishing permanent electrical contact therebetween, said nut-forming element defining an axial bore through which said electrode member passes and rotates, said nut-forming element and said electrode member having cooperating means mating with one another for effecting axial movement of said electrode member in said bore and relative to said insulating housing upon rotation of said electrode member by said control means; and means for electrically connecting said electrical conductor to said nut-forming element.

* * * * *